United States Patent [19]
Mitchell et al.

[11] Patent Number: 5,642,370
[45] Date of Patent: Jun. 24, 1997

[54] HIGH REPETITION RATE ERBIUM; YAG LASER FOR TISSUE ABLATION

[75] Inventors: Gerald M. Mitchell, Los Altos; Edward D. Reed, Sunnyvale; Greg J. Spooner, Palo Alto; Michael Hmelar, Palo Alto, all of Calif.

[73] Assignee: Coherent, Inc., Santa Clara, Calif.

[21] Appl. No.: 694,462

[22] Filed: Aug. 12, 1996

Related U.S. Application Data

[63] Continuation of Ser. No. 422,827, Apr. 17, 1995, abandoned.

[51] Int. Cl.⁶ .......................................... H01S 3/10
[52] U.S. Cl. .................. 372/25; 372/108; 372/97; 372/6; 372/34
[58] Field of Search .................... 372/25, 97, 576, 372/34, 70, 107, 108; 606/3, 2, 4, 6, 7; 128/395

[56] References Cited

U.S. PATENT DOCUMENTS

| | | | |
|---|---|---|---|
| 4,521,194 | 6/1985 | Myers et al. | 433/215 |
| 4,744,360 | 5/1988 | Bath | 128/303.1 |
| 4,818,230 | 4/1989 | Myers et al. | 433/215 |
| 4,846,172 | 7/1989 | Berlin | 128/303.1 |
| 4,862,886 | 9/1989 | Clarke et al. | 372/70 |
| 4,988,163 | 1/1991 | Cohen et al. | 350/96.29 |
| 5,005,180 | 4/1991 | Edelman et al. | 372/6 |
| 5,048,034 | 9/1991 | Tulip | 372/107 |
| 5,074,861 | 12/1991 | Schneider et al. | 606/17 |
| 5,112,328 | 5/1992 | Taboada et al. | 606/4 |
| 5,139,494 | 8/1992 | Freiberg | 606/3 |
| 5,222,952 | 6/1993 | Loertscher | 606/6 |
| 5,243,615 | 9/1993 | Ortiz et al. | 372/34 |
| 5,246,435 | 9/1993 | Bille et al. | 606/6 |
| 5,246,436 | 9/1993 | Rowe | 606/4 |
| 5,263,950 | 11/1993 | L'Esperance, Jr. | 606/6 |
| 5,274,728 | 12/1993 | Tran | 385/142 |
| 5,290,274 | 3/1994 | Levy et al. | 606/13 |
| 5,304,167 | 4/1994 | Freiberg | 606/3 |
| 5,342,198 | 8/1994 | Vasiliadis et al. | 433/215 |
| 5,349,590 | 9/1994 | Amirkhanian et al. | 372/6 |
| 5,363,387 | 11/1994 | Sinofsky | 372/25 |
| 5,375,132 | 12/1994 | Connors et al. | 372/34 |
| 5,387,211 | 2/1995 | Saadatmanesh et al. | 606/10 |
| 5,401,171 | 3/1995 | Paghdiwala | 433/215 |
| 5,422,899 | 6/1995 | Freiberg et al. | 372/25 |
| 5,423,798 | 6/1995 | Crow | 606/4 |
| 5,435,724 | 7/1995 | Goodman et al. | 606/3 |

FOREIGN PATENT DOCUMENTS

| | | | |
|---|---|---|---|
| 0335714 | 10/1989 | European Pat. Off. | A61B 17/22 |
| 0575274 | 12/1993 | European Pat. Off. | A61C 1/00 |
| 0626229 | 11/1994 | European Pat. Off. | B23K 26/00 |
| 3233986 | 10/1991 | Japan | H01S 3/06 |
| WO89/11261 | 11/1989 | WIPO | A61F 9/00 |

OTHER PUBLICATIONS

Aesculap Meditec brochure, "The Er:YAG Laser System for ophthalmic microsurgery," Oct. 1994, 2 pages in length.
LaserSight Centers brochure, "CENTAURI™ Ophthalmic Erbium:Yag Laser," Nov. 1993, 1 page in length.

*Primary Examiner*—Leon Scott, Jr.
*Attorney, Agent, or Firm*—Limbach & Limbach L.L.P.

[57] ABSTRACT

A medical laser system is disclosed for ablating biological material. The system includes an Erbium:YAG gain medium capable of generating a pulsed output having a wavelength of 2.9 microns. The laser is optimized to generate a pulsed output having a repetition rate of at least 50 hertz and preferably at least 100 hertz. The output is delivered to the target tissue via an optical fiber. Preferably, a suction source is provided to aspirate the tissue as it is being ablated. The erbium laser system provides accurate ablation with minimal damage to surrounding tissue.

14 Claims, 5 Drawing Sheets

HIGH REPETITION RATE ERBIUM; YAG LASER FOR TISSUE ABLATION

This is a continuation of application Ser. No. 08/422,827, filed on Apr. 17, 1995 now abn.

TECHNICAL FIELD

The subject invention relates to a medical laser system for ablating and emulsifying biological material.

BACKGROUND OF THE INVENTION

In recent years, there has been a significant amount of progress made in developing solid state laser systems for medical applications. Today, commercial systems are available which generate pulsed outputs at a variety of wavelengths. Many of the early solid state medical laser systems were based on neodymium doped gain media which generate a near infrared output wavelength of 1.06 microns. Using specific frequency selective optics, Nd:YAG medical lasers systems have also been developed which generate an output of 1.44 microns. (See, for example, U.S. Pat. No. 5,048,034).

It has been known for some time that tissue ablation can be enhanced through the use of infrared wavelengths that more closely match absorption peaks of water, the major constituent in biological tissue. To this end, the assignee herein (as well as others) have introduced medical laser systems which include a gain medium wherein holmium is the lasing species. These laser systems generate an output wavelength of 2.1 microns. The absorption coefficient in water for 2.1 micron radiation is more than two hundred times greater than the absorption coefficient of 1.06 micron radiation. This greater absorption coefficient means that more energy will be absorbed at the surface of the tissue (rather than penetrating into the tissue) resulting in cleaner ablation with less thermal damage.

One problem with the holmium laser systems is that they cannot easily be configured to generate the same output powers associated with Nd:YAG systems. To address this problem, multiple head laser systems have been developed, wherein each system includes two or more laser resonators, each having a holmium:YAG laser rod. The pulsed outputs of these laser resonators are interleaved and combined along a common output path to generate an output having a higher average power and higher repetition rate. Such system is described in U.S. Pat. No. 5,374,132, issued Dec. 20, 1994, assigned to the same assignee herein and incorporated by reference. (See also, U.S. Pat. No. 5,307,211) While the approach of using multiple resonators has been commercially successful, it is more complex and expensive than using a single resonator.

More recently, the industry has been exploring the use of erbium doped gain media for medical applications. Erbium doped YAG crystals will generate an output wavelength of 2.9 microns which is matched to a prominent absorption peak in water. Radiation at 2.9 microns has an absorption coefficient in water about two hundred times greater than 2.1 micron radiation. While this strong absorption in water would seem to make erbium laser systems the ideal candidate for tissue ablation in medical laser systems, certain problems arose.

One primary problem related to the lack of suitable optical fibers for delivering the 2.9 micron radiation. Common silica based fibers transmit 2.9 micron radiation with very low efficiency. Fluoride based fibers, which attenuate the 2.9 micron radiation to a much lesser extent than silica fibers, are relatively toxic to the human body. More recently, improvements in the fiber delivery technology have made the use of erbium laser light more viable.

Efforts have also been made to increase the pulse repetition rate of erbium laser systems having a single resonant cavity. Quite recently, a system was introduced which could generate a pulsed output at a maximum rate of 30 Hertz. Unfortunately, attempts to increase the repetition rate even higher result in a significant reduction in output power as well as an increase in the thermal loading of the laser rod leading to instabilities.

SUMMARY OF THE INVENTION

The subject invention is based, in part, on the recognition that the extremely high coefficient of absorption of 2.9 micron radiation in water allows tissue to be cleanly ablated, vaporized and/or incised at relatively low energy levels per pulse. Moreover, it has been recognized that ablation efficiency can be dramatically enhanced if a relatively high pulse repetition rate is used, even if the energy per pulse is relatively low. Optimal performance can also be enhanced by utilizing a delivery system which functions to simultaneously aspirate the tissue as it is being ablated or emulsified.

In initial experiments, the speed at which certain tissue ablation and incision procedures were performed was vastly increased using a high repetition rate, low energy per pulse, Er:YAG laser. For example, the subject laser was utilized to perform a photophacoemulsification, a common ophthalmic procedure where the lens in the eye is ablated. This procedure can take a number of minutes using a mechanical device. In contrast, using the subject erbium laser, this procedure was performed in less than 40 seconds. Other examples will be discussed below.

In accordance with the subject invention, a system is provided which includes an erbium doped, solid state gain medium mounted in a resonant cavity. The gain medium is excited by a flashlamp which is energized with a power supply. The power supply is controlled in a manner to generate a pulsed output of at least 50 hertz, and preferably greater than 100 hertz. At this repetition rate, high precision, high speed tissue ablation and smooth, fluid incisions can be achieved.

It is believed that the threshold for ablating or incising biological material can be as low as 0.5 millijoules per pulse delivered to the tissue. By optimizing the design of the laser system, it is believed that high repetition rates can be achieved while still maintaining reasonable output powers, on the order of 50 to 150 millijoules per pulse at the output coupler. At this level, the energy density needed for tissue ablation and incision can easily be delivered to the treatment site.

In one significant aspect of the subject invention, the reflectivity of the output coupler has been increased with respect to a conventionally optimized system. Increasing the reflectivity of the output coupler reduces the slope efficiency of the laser which would be a concern if the laser were to be operated at high powers. Of more importance, increasing the reflectivity of the output coupler also functions to reduce the threshold input for achieving lasing action. By this arrangement, lower input powers may be used which permits the pulse repetition rate to be increased without causing the laser to become unstable.

Another modification which can be employed to enhance the performance of the laser is to provide concave surfaces on the ends of the gain medium. These concave surfaces function to counteract the focusing effects associated with thermal lensing in the rod. It may also be desirable to include selective filters between the flashlamp and gain medium to reduce exposures to light energy which merely serves to heat the gain medium, rather than contributing to the excited states.

Additional details about the subject invention and its method of use will become apparent from the following detailed description, taken in conjunction with the drawings, in which:

DETAILED DESCRIPTION OF THE PREFERRED EMBODIMENTS

Figure 1:
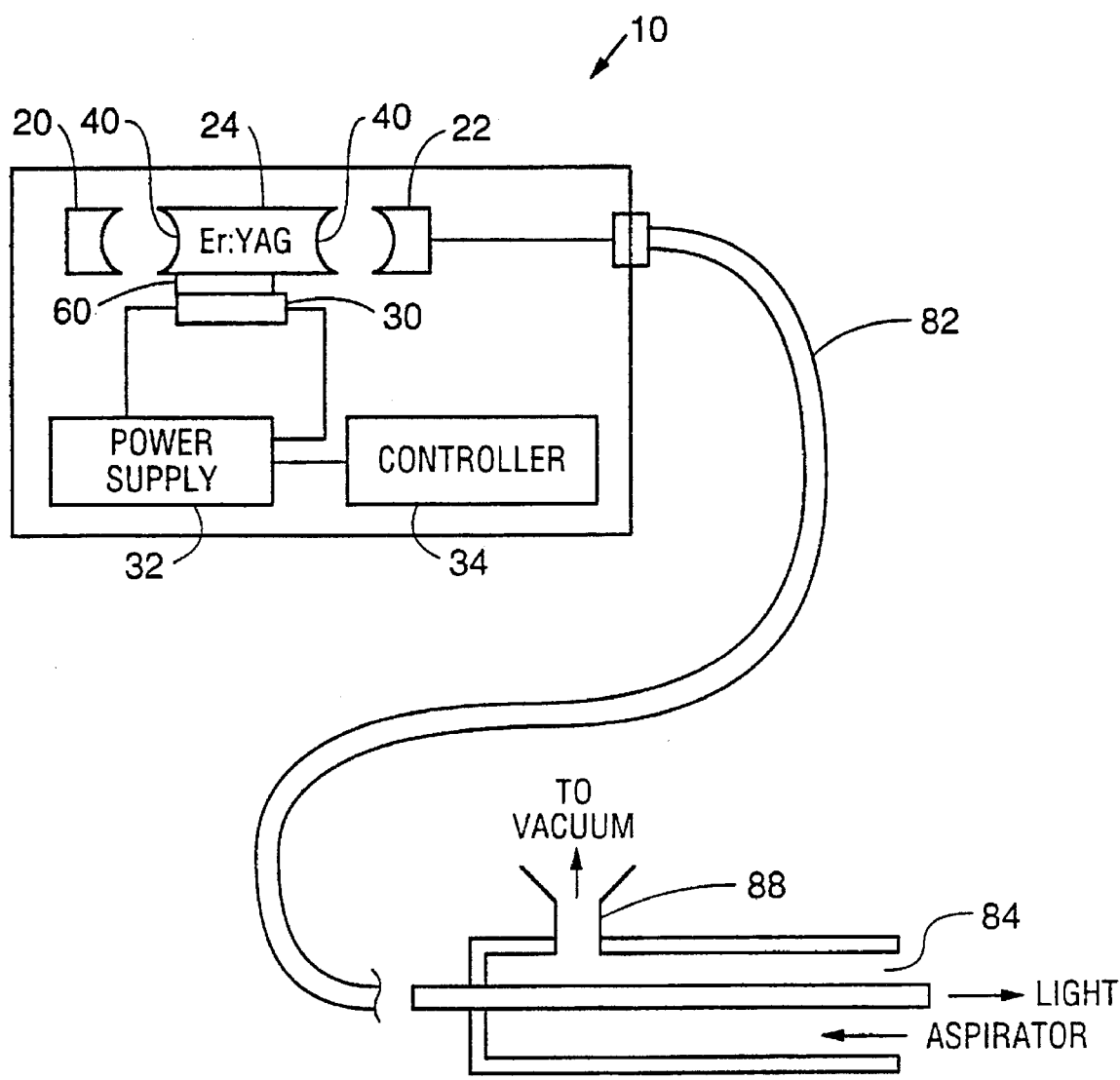
FIG. 1 is a schematic diagram of a medical laser system formed in accordance with the subject invention.

FIG. 1 illustrates a laser system 10 formed in accordance with the subject invention. Laser system 10 includes a laser head consisting of a resonant cavity defined by a high reflecting mirror 20 and a partially reflecting output coupler 22. A gain medium 24 is positioned within the resonant cavity. Gain medium 24 is defined by an erbium doped solid state crystal. The most common erbium doped crystal is Er:YAG which generates an output wavelength of 2.9 microns. Another common host crystal is YSGG which when, doped with erbium, will generate an output of 2.8 microns.

The gain medium 24 is excited by a flashlamp 30. The gain medium and flashlamp are preferably mounted in a closely coupled cavity of the type described in U.S. Pat. No. 5,375,132. This type of cavity can include a jacket formed from $BaSO_4$ acting as a diffuse reflector and maximizing the efficiency of the flashlamp 30.

The flashlamp is energized by a power supply 32. The power supply 32 is connected to a conventional controller 34 which may include a microprocessor with external inputs.

In accordance with the subject invention, the controller and power supply are operated in a manner to generate a pulsed laser output at a high repetition rate. In the preferred embodiment, the laser is operated at a minimum of 50 hertz, and preferably at least 100 hertz.

In order to insure stable operation at this high repetition rate, a number of laser parameters must be properly optimized. First, the length of activation of the flashlamp pulses should be on the order of 100 to 200 microseconds. The output pulses from the laser will typically be about thirty percent shorter than the flashlamp pulses. In addition, it would be desirable to reduce the average input power to the gain medium to minimize thermal loading and the associated thermal lens effects.

The principal approach which is used in the subject system to reduce the average input power is to increase the reflectivity of the output coupler. In a typical erbium laser system, an output coupler having ten percent transmission might be selected in order to maximize the slope efficiency, and produce a relatively high output power for a given input power. In the subject laser system, the transmission of the output coupler is reduced to between eight and two percent and in the preferred embodiment, is set at four percent.

Figure 2:
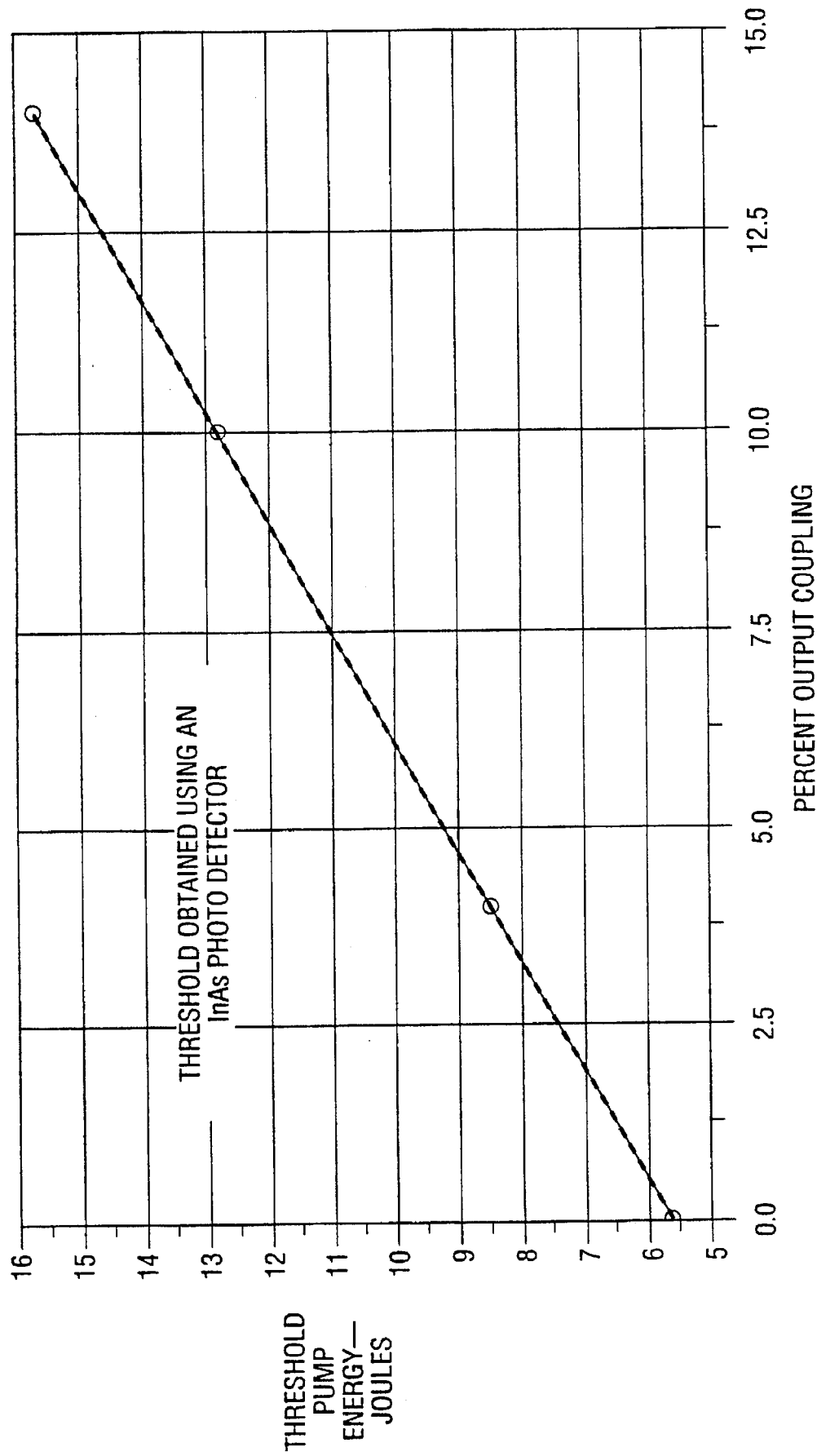
FIG. 2 is graph illustrating the variation in threshold pump energy as a function of the percentage output coupling which is used in the laser.

FIG. 2 is a graph plotting data which was obtained in some early experiments and illustrates the threshold pump energy as a function of the transmission level of the output coupler in an erbium laser. As can be seen in this graph, where the output coupling was set at ten percent transmission, the threshold pump energy was close to 13 joules. However, by reducing the transmission of the output coupler to only four percent, the threshold was also be reduced to under 9 joules. In the preferred design discussed below, the lasing threshold has been reduced to 5 joules input power.

As is well known, reducing the transmission of the output coupler also reduces the efficiency of the laser so that more energy would be needed to generate high energy output pulses. However, and as noted above, it has been recognized that clean ablation, incision or emulsification can be achieved with relatively low energy pulses (i.e. 100 millijoules or less at the output coupler and as little as 0.25 to 0.5 millijoules delivered to the tissue). By reducing the transmission of the output coupler, it is possible to obtain the desired output pulse energy with significantly lower energy input pulses. Having a lower input energy per pulse, allows the repetition rate to be increased without exceeding the maximum average input power level associated with thermal instability. In the preferred embodiment, the input energy per pulse ranges from five to 20 joules. At an input of five joules, lasing will just be initiated. If the system is properly optimized with the procedures discussed below, a stable output of up to 150 millijoules per pulse at the output coupler can be generated with an input energy to the flashlamp of 20 joules.

To further enhance the stability of the laser and allow operation at higher repetition rates and input powers, it is also desirable to provide correction for the thermal lensing effects in the resonant cavity. In the preferred embodiment, this result is achieved by providing the ends 40 of the gain medium with a concave configuration. The concave configuration, which can be a spherical surface having a 20–30 cm radius, provides a pair of lenses with negative focal powers in the cavity which offset the positive thermal lens formed in the gain medium.

Figure 3:
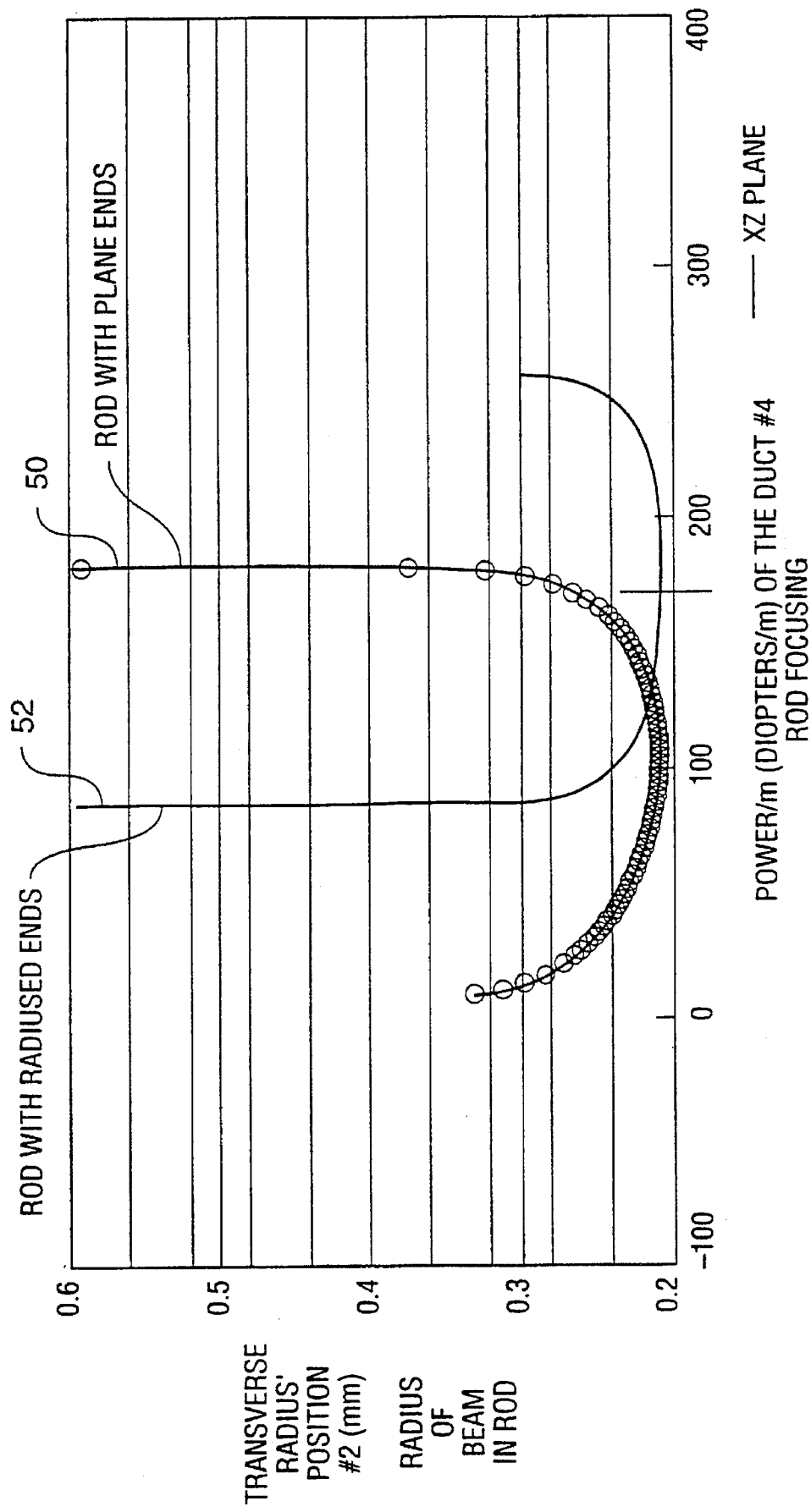
FIG. 3 is a graph illustrating the improvements in stability which can be achieved using curved end faces on the solid state gain medium.

FIG. 3 illustrates the benefits which can be achieved using radiused end surfaces on the gain medium. FIG. 3 illustrates the variation of the radius of the laser beam within the rod as a function of the strength of the positive thermal lens in the rod. The curves in FIG. 3 illustrate the stability regions of the laser. Curve 50 illustrates a rod with flat end surfaces and demonstrates that the center of the stability curve occurs when the thermal loading on the rod creates a thermal lens of 100 diopters per meter in strength. Curve 52 illustrates a rod with radiused ends. As can be seen, providing the rod with radiused ends shifts the stability curve in a manner such that the center of the curve 52 occurs at about 160 diopters per meter of thermal lensing which corresponds to significantly higher thermal loads. A laser having a gain medium with radiused ends can be operated with higher energy input pulses and at a higher repetition rate without becoming unstable.

There are other approaches which can be used to further enhance stability. For example, a bandpass filter 60 can be provided between the flashlamp and the gain medium. The filter can be formed from a material which will transmit radiation which most efficiently excites the erbium lasing transitions and absorbs high energy photons which primarily heat the crystal.

Figure 4:
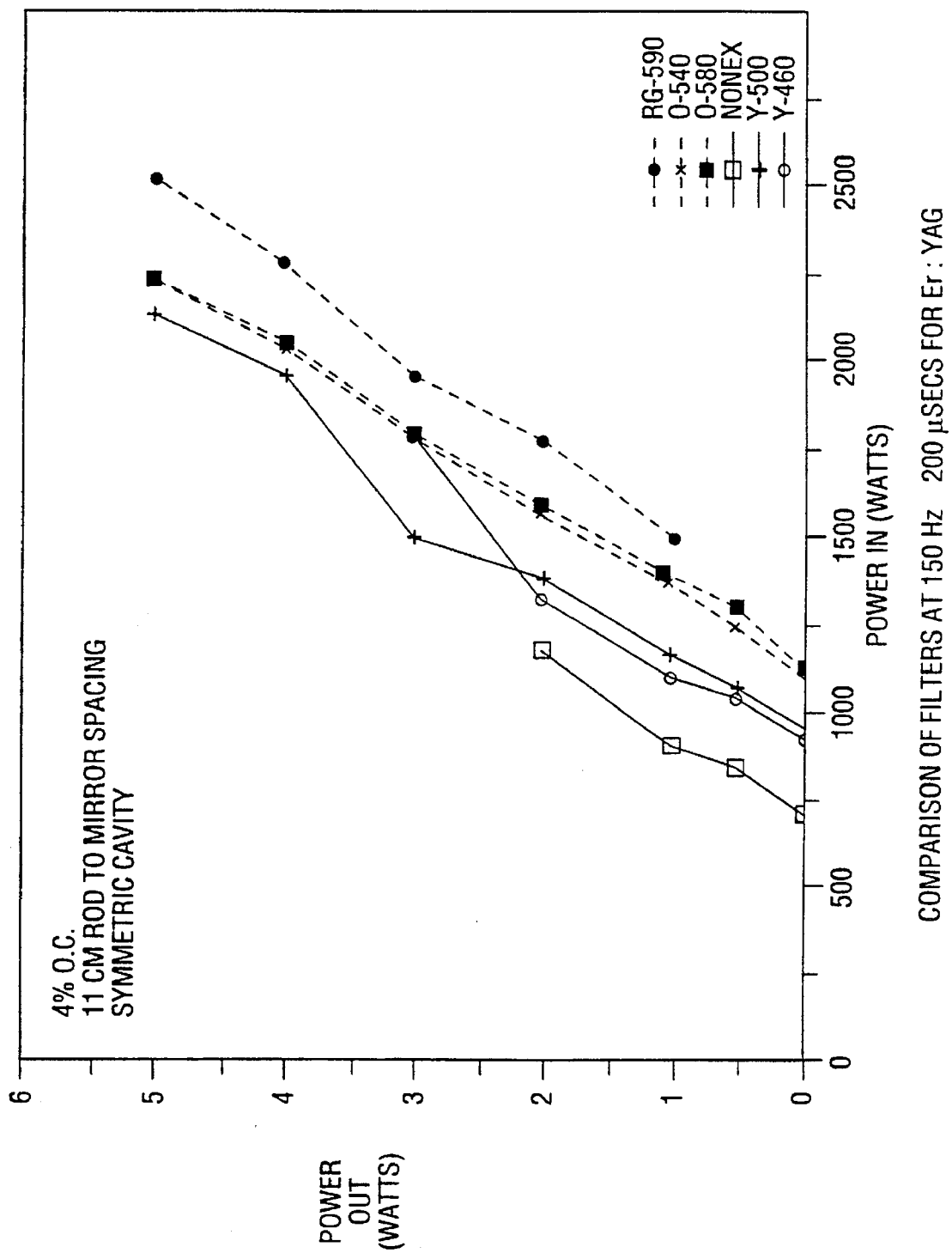
FIG. 4 is a graph illustrating the use of various optical elements having different transmission characteristics to filter the light reaching the gain medium from the flashlamp.

FIG. 4 is a graph illustrating the changes in performance which can be achieved using different filters. The graph plots the average output power from the laser as a function of input power. The data was taken for a laser operating at a repetition rate of 150 hertz and an output coupler with a four percent transmission level.

Each of the filters illustrated are "cut-off" filters which transmit most of the light above a certain wavelength and absorb most of the light below that wavelength. The filter identified as "Nonex" is soda lead borosilicate glass from Corning (glass code 7720) that has a cut-off at roughly 400 nanometers. The remainder of the filters are colored glasses (O=orange; Y=yellow) having cut-offs at the wavelengths indicated by the number following the letter code.

As can be seen, at low powers, the Nonex filter is highly efficient, permitting the generation of the most output power for a given input power. However, at higher input powers, a laser using the Nonex filter became unstable.

As can be appreciated, the selection of a particular filter will be based upon the desired operating parameters. In general, the filter selected will permit high output powers to be generated without the laser becoming unstable due to thermal lensing, while at the same time, minimizing the input power necessary to achieve a given output power. In the graph of FIG. 4, the filters identified as O-580 and Y-500 are good choices to maximize output power while minimizing thermal lensing effects for the tested laser operating at 150 hertz.

It should be pointed out that the various specific, individual concepts discussed above for optimizing the subject erbium laser system are not, in and of themselves new. For example, it is known that providing radiused ends on a gain medium can help to compensate for thermal lens effects. Similarly, it is known that filtering a flashlamp can increase the efficiency of a laser system. (See U.S. Pat. No. 5,243,615 issued Sep. 7, 1993 to Ortiz). However, it is believed these approaches have not been combined and utilized to provide a substantial increase in the repetition rate of an erbium laser system in a manner to provide significantly more effective and high speed ablation of biological material.

In the most current prototype of the subject invention, the laser includes an Er:YAG rod 4 mm in diameter and 90 mm in length and the ends of the rod are provided with concave, radiused ends having a curvature of 30 cm. The resonator mirrors have a slight radius (one meter curvature) but could be planar. The resonator is symmetric with the mirrors being equally spaced from the ends of the rod by 11 cm for a total resonator length of 31 cm. A Xenon flashlamp was used and operated at 100, 150 and 200 hertz repetition rate.

In addition to maximizing the repetition rate generated by a single laser head, further enhancements can be achieved using multiple laser heads and time multiplexing the output pulses. There are many examples of such approaches in the prior art including the designs set forth in U.S. Pat. Nos. 5,374,132, and 5,307,211 cite above. This type of system is generically illustrated in FIGS. 5 and 6.

Figure 5:
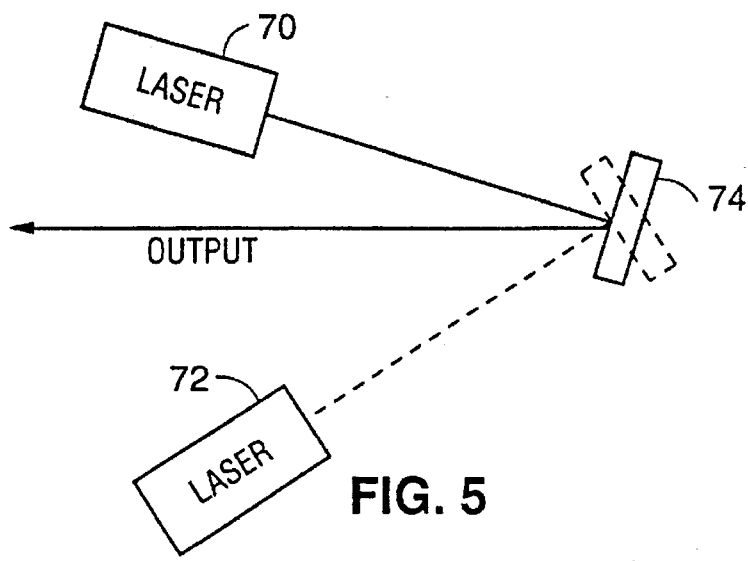
FIG. 5 is a schematic diagram of a laser system having two resonant cavities which can generate higher pulse repetition rates using a time-multiplexed output.
Figure 6:
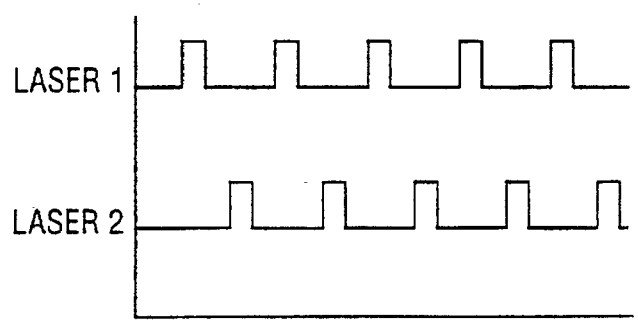
FIG. 6 is a graph illustrating the time-multiplexed output which can be used in the laser system of FIG. 5.

In these type of systems, the output of two or more lasers 70 and 72 are combined along a common output path using some form of optical combiner. In FIG. 5, a tilting mirror or galvanometer 74 is shown. The controller to the power supplies of the lasers 70 and 72 is configured so that both lasers will generate an alternating, pulsed output. For example, and as schematically illustrated in FIG. 6, both lasers can be configured to generate a pulsed output at 100 hertz. However, the timing of the pulses is arranged so that when one laser is generating a pulse, the other laser is not. The moving mirror 74 can be used to interleave the pulses to generate an output train at 200 hertz.

Mirror 74 is arranged to tip back and forth between two positions. In a first position (shown in solid line of FIG. 5), the mirror reflects the output beam from laser 70 along the common output path. After the output pulse from laser 70 is finished, mirror 74 will move to the second position (shown in phantom line) where it can reflect the output pulse from laser 72 along the common output path. The mirror will continue to move back and forth between the two positions to generate the desired output stream.

Figure 7:
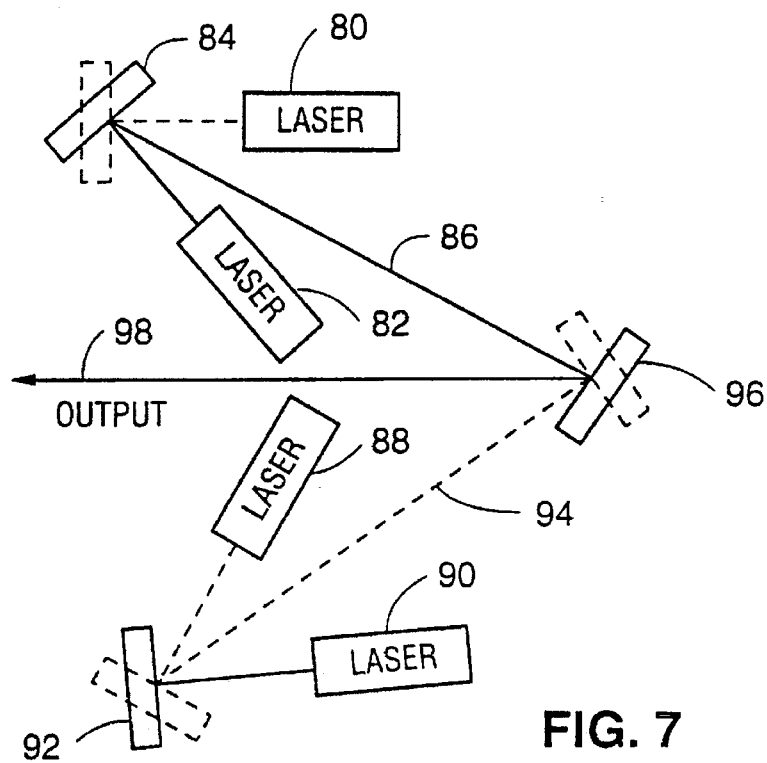
FIG. 7 is a schematic diagram of a laser system having four resonant cavities which can generate still higher pulse repetition rates using a time-multiplexed output.

FIG. 7 illustrates how the concept of combining multiple outputs could be expanded to four laser resonators. As shown therein, the output from a first pair of laser resonators (80 and 82) can be combined by a galvanometer mirror 84 along a first, intermediate output path 86 in the same manner as shown in FIG. 5. Similarly, the output from a second pair of laser resonators (88 and 90) can be combined by a second galvanometer mirror 92 along a second, intermediate output path 94. The outputs directed along the two intermediate paths can then be combined by third galvanometer mirror 96 along a main common output path 98. Using this approach, the repetition rate of the final output train will be four times higher than the repetition rate for each of the individual laser resonators.

Various other optical beam combiners can be used to multiplex the output of a plurality of pulsed lasers. For example, U.S. Pat. No. 5,307,211 describes the use of a spinning disc having reflective and transmissive quadrants. U.S. Pat. No. 5,374,132 describes the use of a spinning angled reflector.

Since the use of multiple laser heads and time-multiplexing can add costs and complexity to the system, it is believed preferable to initially maximize the pulse repetition rate that can be obtained from a single laser head. If still higher pulse repetition rates are desirable, then the pulsed output of multiple heads which have been individually optimized can be combined in the manner described above.

As described above, the intent of the subject invention is to provide a laser system particularly suited for ablation, precise, continuous incisions, vaporization and/or emulsification of biological material. To further facilitate this goal, it has been found desirable to combine the lasing action with aspiration at the treatment site. One type of mechanism for achieving this result is illustrated in FIG. 1.

As shown therein, the light output from the erbium laser is coupled out of the housing 80 into an optical guide 82 which can be defined by an optical fiber. One type of fiber which is suitable for carrying erbium laser light with reduced attenuation includes germanium oxide Type IV fiber. Such a fiber is described in U.S. Pat. No. 5,274,728 issued Dec. 28, 1993 to Tran and is manufactured by IFS Systems. Sapphire fibers can also be used to transmit erbium radiation. Sapphire fibers are available from Saphikon.

It would also be possible to deliver the light through hollow waveguides. Such waveguides often include multilayer dielectric coatings to enhance transmission. It may also be desirable to deliver the erbium laser light through an articulated arm of the type typically used to deliver the treatment beam in a carbon dioxide medical laser system. An articulated arm delivery system will be necessary if the power of the treatment beam is greater than the power density handling characteristics of the optical fibers.

The distal end of guide 82 feeds into a probe 84 which is designed to be placed next to the region of biological tissue to be ablated. At the present time, there exist a large number of different types of delivery probes, many of which are specifically designed for specific medical procedures. FIG. 1 is intended to illustrate a generic probe. As can be seen, the guide 82 is mounted within the probe. A channel 84 is also provided within the probe and communicates with a vacuum source through fitting 88.

During use, the vacuum source can be employed to aspirate material which has been fragmented or emulsified by the pulsed erbium laser light. The vacuum source can also be used to draw the tissue into close proximity with the delivery end of the guide thereby facilitating its destruction.

It is believed that the subject, high repetition rate, high precision erbium laser system, which generates an output wavelength which is highly absorbed in tissue, can be used in a number of procedures to improve the ablation, incision, vaporization and emulsification of biological tissue. Some preliminary experiments have already been performed with a prototype system to confirm these beliefs.

One of the principal fields which can benefit from the use of the subject system will relate to ophthalmic applications. For example, one common ophthalmic procedure requires the removal of a lens having cataracts. The common approach for performing this removal is to use an ultrasonic device which is inserted into the eye for breaking the lens into small pieces. The small pieces are then aspirated. This procedure will typically take several minutes to perform. This procedure must be done very carefully to insure that endothelium of the eye is not compromised.

In accordance with the subject invention, a lens can be emulsified using the pulsed output from the erbium laser. As noted above, the ablation threshold of tissue is quite low, so only relatively low powers are necessary. In an initial experiment using an erbium laser operating at 100 hertz, a cadaver lens was completely emulsified and aspirated in only 37 seconds. Even faster emulsification rates were achieved using a laser system operating at 200 hertz.

Another advantage to the high repetition rate erbium laser is that the temperature rise in the tissue is much lower then would be encountered in an ultrasonic procedure such that the potential for damage of the epithelium is minimized. In this regard, it should be noted that the high absorption and short penetration depth of 2.9 micron light in tissue means that the destructive radiation can be accurately targeted and heating will not spread beyond the treatment region. These attributes make the high repetition rate erbium laser extremely attractive for use with fragile tissue typically encountered in the eye.

Another ophthalmic procedure which would be a good candidate for the subject high repetition rate erbium laser would be photovitrectomy. In this procedure, the vitreous in the eye must be removed. This procedure is presently performed using a mechanical chopper. In initial experiments with the high repetition rate erbium laser, the vitreous can be emulsified and removed at least ten times faster than with a mechanical system.

One particular benefit to this approach is that the aspirating channel 84 can be made much smaller than would be necessary in a mechanical procedure. In a mechanical procedure, the vitreous is chopped into pieces which must fit within the channel. In contrast, with an erbium laser, the vitreous is emulsified or liquified and can be sucked into a small bore. The benefit of a small bore is that it will prevent unwanted material from being sucked into the probe. In addition, in a mechanical procedure, strands of vitreous are sometimes sucked into the probe. These strands are attached to the eye and can tug on fragile tissue such as the retina, causing severe damage. In contrast, the erbium laser immediately emulsifies the ends of the strands so that strands will not be tugged towards the probe by the suction force.

Other ophthalmic procedures which may benefit from the subject high repetition rate erbium laser include capsulotomies, sclerostomies, excision of pupillary membranes, cutting of vitreous bands and iris margin and strand trim work. The high precision of this system could be used effectively in refractive surgery, creating drains when treating chronic glaucoma, clearing tear ducts and scleral cyst removal.

It is believed that high repetition rate erbium systems will be beneficial in medical applications which have previously been performed with lower repetition rate systems. For example, there has been significant experimental work performed investigating the application of erbium laser light in dental applications. The applications include drilling teeth, removal of carries, etc. The erbium laser will also be useful for shaping and or removing bones and connective tissue such as cartilage, ligaments and tendons. The erbium laser system can also be used to open passages that pinch nerves, remove pathologic matter caused by Osteoarthritis and for spine disk modification (percutaneous discectomy).

Since the erbium wavelength generates only minimal thermal damage beyond the treatment region, it should also be useful in procedures which need an extremely high degree of position accuracy. One such application will include the shaving of material adjacent to the nervous system as well as brain tissue removal and treating brain abscesses. Similarly, the erbium system could be used for inner ear operations including stapedectomies and maxillary sinus osteotomies.

The erbium laser system could also be used for targeted removal of cancerous tissue and/or tumors in the gall bladder, larynx, liver, glands, pancreas, lungs, stomach, thyroid and trachea. The system could also be used for organ removal such as in a hysterectomy and in gall bladder removal. The laser could also be used to remove fatty tissue (liposuction).

The erbium laser system can be used in a variety or urinary organ procedures such as kidney wall modification, stone (calculi) fragmentation and removal in the kidney, gall bladder and ureter (lithotripsy), transurethral incision of the prostate, prostatectomy, ureter lesion removal, vasal tissue removal, nephrectomy, vasovasotomy and lymph node modification. In the vascular system, the high repetition rate, precision erbium laser system could be used to open strictures in the aorta, modify vessels at an aneurysm, for clearing vessels (angioplasty) and clot removal (clearing a hematoma).

It is envisioned that most of the above described surgical procedures will be performed in a liquid field. It is known that if sufficient pulse energies are used, vapor bubbles will be formed in the liquid medium. The vapor bubbles are formed due to the high absorption of the erbium laser wavelength in water. The creation and subsequent collapse of the vapor bubble creates an acoustic shock wave which can further enhance the ablation effects of the system.

It is also possible to use the erbium laser in a dry or air field. Operating in a dry field will be particularly desirable where the tissue is fragile and destruction due to acoustic effects should be minimized. For example, if the subject erbium laser system is used to ablate tissue associated with the nervous system, it may be desirable to work in air thereby providing the most precise and accurate ablation. In this manner, the less targeted destruction associated with the acoustic effects can be avoided.

In summary, there has been disclosed a medical laser system for ablating biological material. The system includes a high repetition rate erbium laser generating a pulsed output having a wavelength of 2.9 microns. The pulsed output is generated at a rate of at least 50 hertz and preferably at least 100 hertz. The output can be used to ablate or emulsify tissue quickly with minimal thermal damage.

While the subject invention has been described with reference to the preferred embodiments, various changes and modifications could be made therein, by one skilled in the art, without varying from the scope and spirit of the subject invention as defined by the appended claims.

We claim:

1. A laser system for treating biological material comprising:

a resonant cavity having an output coupler;

an erbium doped solid state gain medium located within said cavity;

a flashlamp for periodically exciting said gain medium to generate laser output pulses;

power supply for energizing said flashlamp;

means connected to and controlling said power supply and functioning to generate a pulsed output to said flashlamp at a predetermined repetition rate and duration and wherein the transmission of the output coupler is selected to control the energy threshold input for lasing and wherein the cavity design parameters are selected to compensate for thermal lens effects such that stable laser output pulses having a repetition rate of at least 50 hertz are generated; and means for delivering said pulsed output to said biological tissue to cut, vaporize, ablate incise or emulsify the tissue.

2. A system as recited in claim 1 wherein each of said output pulses has an energy of at least 50 millijoules.

3. A system as recited in claim 1 wherein each of said output pulses has an energy of at least 100 millijoules.

4. A system as recited in claim 1 wherein the energy of each of said output pulses delivered to the tissue is at least 0.5 millijoules.

5. A system as recited in claim 1 wherein said resonant cavity includes a partially reflecting mirror defining an output coupler and wherein percentage transmission of the output coupler at the wavelength of the output pulses is less than eight percent.

6. A system as recited in claim 5 wherein the reflectivity of the output coupler is at least two percent.

7. A system as recited in claim 5 wherein the reflectivity of the output coupler is four percent.

8. A system as recited in claim 1 wherein the gain medium has an optical axis and two opposed end surfaces, and wherein the end surfaces are provided with concave configurations to reduce the effects of thermal lensing in the gain medium.

9. A system as recited in claim 1 further including a means associated with the delivery means for aspirating the material being vaporized from the treatment site.

10. A system as recited in claim 1 wherein the repetition rate of the output pulses is at least 75 hertz.

11. A system as recited in claim 1 wherein the repetition rate of the output pulses is at least 100 hertz.

12. A system as recited in claim 1 wherein said delivery means includes an optical fiber.

13. A system as recited in claim 1 further comprising:

a second resonant cavity;

a second erbium doped solid state gain medium located within said second cavity;

a second flashlamp for periodically exciting said second gain medium to generate output pulses, said second flashlamp being connected to said power supply and said control means; and means for combining the pulsed output from said cavities along a common optical axis and into said delivery means and wherein said control means functions to alternately energize said flashlamps so that a pulsed output is generated at twice the repetition rate of the pulsed output from each individual resonant cavity.

14. A system as recited in claim 1 further comprising:

a plurality of resonant cavities, with each said cavity including an erbium doped solid state gain medium located therein;

optical means for periodically exciting the gain media to generate output pulses, said optical means being connected to said power supply and said control means; and means for combining the pulsed output from said cavities along a common optical axis and into said delivery means and wherein said control means functions to sequentially excite said gain media so that a pulsed output is produced at a repetition rate which represents the combined pulsed output from each individual resonant cavity.

* * * * *